United States Patent
Gardarsson et al.

(10) Patent No.: US 10,238,124 B2
(45) Date of Patent: Mar. 26, 2019

(54) APPARATUS AND A METHOD FOR PRODUCING A MIX OF AT LEAST TWO FOOD PRODUCTS WHERE THE MIX FULFILS AT LEAST TWO TARGET CRITERIA

(71) Applicant: Marel Iceland Ehf, Gardabaer (IS)

(72) Inventors: Saevar Gardarsson, Mosfellsbaer (IS); Skuli Sigurdsson, Kopavogur (IS); Brynjolfur Thorsson, Reykjavik (IS)

(73) Assignee: MAREL ICELAND EHF, Gardabaer (IE)

( * ) Notice: Subject to any disclaimer, the term of this patent is extended or adjusted under 35 U.S.C. 154(b) by 108 days.

(21) Appl. No.: 14/647,980

(22) PCT Filed: Dec. 13, 2013

(86) PCT No.: PCT/EP2013/076581
§ 371 (c)(1),
(2) Date: May 28, 2015

(87) PCT Pub. No.: WO2014/091006
PCT Pub. Date: Jun. 19, 2014

(65) Prior Publication Data
US 2015/0296813 A1     Oct. 22, 2015

Related U.S. Application Data

(60) Provisional application No. 61/737,196, filed on Dec. 14, 2012.

(30) Foreign Application Priority Data

Dec. 14, 2012 (DK) .................................. 2012 70786

(51) Int. Cl.
*A22C 5/00* (2006.01)
*A22C 18/00* (2006.01)
(Continued)

(52) U.S. Cl.
CPC .............. *A22C 18/00* (2013.01); *A22C 5/00* (2013.01); *A22C 17/002* (2013.01);
(Continued)

(58) Field of Classification Search
CPC ......... A22C 5/00; A22C 18/00; A22C 17/002; A22C 17/0073–17/008; A22C 17/0093;
(Continued)

(56) References Cited

U.S. PATENT DOCUMENTS 3,050,399 A * 8/1962 Kielsmeier ............. A23L 13/65
426/231
4,171,164 A * 10/1979 Groves .................. G01N 23/14
366/152.1
(Continued)

FOREIGN PATENT DOCUMENTS

WO        0021376 A1     4/2000

OTHER PUBLICATIONS

PCT International Search Report; Applicant: Marel Iceland Ehf; International Application No. PCT/EP2013/076581; Date of Actual Completion of International Search; Mar. 19, 2014; Date of Mailing of International Search Report: dated Mar. 28, 2014.
(Continued)

*Primary Examiner* — Drew E Becker
(74) *Attorney, Agent, or Firm* — Workman Nydegger

(57) ABSTRACT

Provided is an apparatus and a method for producing a mix of a first type of food products and a second type of food products that fulfills at least two target criteria including a desired weight ratio between the first and second type of food products and a lean/fat ratio of the mix. At least three controllable in-feed channels at an in-feed end of a conveyor supply separate streams of the first and second food products. One of the in-feed channels supplies the first type of food products and two of the in-feed channels supply a
(Continued)

second type of food products being distinguished via a different lean/fat ratio estimate. The determined weight of food products and the measured lean/fat ratio of the food products are used as operation parameters so that the mix fulfills the at least two target criteria.

19 Claims, 2 Drawing Sheets

(51) Int. Cl.
    *A22C 17/00*      (2006.01)
    *B01F 15/00*      (2006.01)
    *B01F 15/04*      (2006.01)
    *G01N 33/12*      (2006.01)
    *G05B 15/02*      (2006.01)
    *A23L 13/60*      (2016.01)

(52) U.S. Cl.
    CPC ........ *A22C 17/008* (2013.01); *A22C 17/0026* (2013.01); *A22C 17/0093* (2013.01); *A23L 13/60* (2016.08); *B01F 15/00194* (2013.01); *B01F 15/00207* (2013.01); *B01F 15/00292* (2013.01); *B01F 15/0408* (2013.01); *B01F 15/0425* (2013.01); *B01F 15/0445* (2013.01); *G01N 33/12* (2013.01); *G05B 15/02* (2013.01); *A23V 2002/00* (2013.01)

(58) Field of Classification Search
    CPC ......... G01N 33/12; A23L 13/60; G05B 15/02; B01F 15/0425; B01F 15/0408; B01F 15/00207; B01F 15/00194; B01F 15/00292; B01F 15/04–15/0495
    USPC .................................. 426/519, 231
    See application file for complete search history.

(56) References Cited

U.S. PATENT DOCUMENTS

| | | | | |
|---|---|---|---|---|
| 5,585,603 | A * | 12/1996 | Vogeley, Jr. | G01G 9/005 177/1 |
| 6,267,661 | B1 * | 7/2001 | Melville | A22B 5/0064 452/155 |
| 7,290,682 | B2 * | 11/2007 | Harra | A23G 9/20 222/135 |
| 2002/0075755 | A1 | 6/2002 | Huber et al. | |
| 2003/0091144 | A1 * | 5/2003 | Bartle | G01N 33/12 378/53 |
| 2004/0081275 | A1 * | 4/2004 | Ostergaard | G01N 23/06 378/57 |
| 2005/0096853 | A1 * | 5/2005 | Hansen | G01N 21/274 702/28 |
| 2005/0255223 | A1 * | 11/2005 | Morin | A22C 5/00 426/646 |
| 2005/0287252 | A1 * | 12/2005 | Schrock | G01N 23/06 426/231 |
| 2006/0154588 | A1 | 7/2006 | Evers | |
| 2009/0080607 | A1 * | 3/2009 | Hoffmann | A22C 5/00 378/53 |
| 2010/0282833 | A1 | 11/2010 | Thorsson et al. | |
| 2013/0199971 | A1 * | 8/2013 | Thorsson | A22C 17/008 209/589 |

OTHER PUBLICATIONS

Danish Search Report; Application No. PA 2012 70786; Date of Completion of Search Report: Jul. 2, 2013.
Australian Office Action from AU Application No. 2013357211, dated Sep. 14, 2017.

* cited by examiner

APPARATUS AND A METHOD FOR PRODUCING A MIX OF AT LEAST TWO FOOD PRODUCTS WHERE THE MIX FULFILS AT LEAST TWO TARGET CRITERIA

CROSS-REFERENCES TO RELATED APPLICATIONS

This application is the national phase of International Application No. PCT/EP2013/076581 filed on Dec. 13, 2013, which claims the benefit of priority to Danish Patent Application No. PA 2012 70786 filed on Dec. 14, 2012 and U.S. Provisional Patent Application No. 61/737,196 filed on Dec. 14, 2012. The entire disclosures thereof are incorporated herein by reference.

FIELD OF THE INVENTION

The present invention relates to an apparatus and a method for producing a mix of a first type of food products and at least one second type of food products so that the mix fulfils at least two target criteria including weight ratio criterion indicating the weight ratio between the first and the at least one second type of food products in the mix and lean/fat ratio criterion of the mix.

BACKGROUND OF THE INVENTION

Ground products such as ground beef, ground lamb, ground pork etc. are sometimes mixed where the mix must fulfill pre-determined target criterion, such as product 1/product 2 weight ratio target and lean/fat target ratio. As an example, one type of mix can be that a customer orders a mix where 60% of the total weight is ground beef and 40% of the total weight is ground pork and where additionally the lean/fat ratio of the mix is 12%.

An important and relative complex factor in grinding meat is keeping the temperature down on the meat. A common way of doing so is to use $CO_2$ or another gas to cool down the meat. The problem with this method is however that this stresses the surface of the product at the cost of the quality.

Another way of keeping the temperature down in ground meat is to use frozen trim, which is typically cheaper than fresh trim. An example of such mix is where a customer orders a ground beef mix where certain percentage of the mix is frozen trim, e.g. 40%, and a certain percentage fresh trim, e.g. 60%, with a certain target lean/fat ratio. The most common way to produce such a mix is to manually mix fresh and frozen trim based on visual lean (VL) that has been determined by an operator prior in the process. This mix is then pre-grinded and a portion is made, e.g. 1000 kg portion. After that, one or more samples are taken from the pre-grind portion to determine the accurate lean/fat ratio level, sometimes referred to as a chemical lean (CL) level. In case of a non-match between the CL and VL levels, the operator must adjust the mix manually so as to reach the desired CL level.

The problem with this process is that the VL level can sometimes be very inaccurate and therefore it may take some time until the CL level of the mix is within the lean/fat ratio range required by the customer. This can therefore obviously be a very time consuming process which is reflected in less throughput of the process. Moreover, if the customer additionally requires a weight target, e.g. 1000 kg of the mix, it may be very difficult to reach such a target value and simultaneously the target CL level.

The inventor of the present invention has appreciated that there is thus a need for a more advanced system of producing a mix of such two or more food products and has in consequence devised the present invention.

SUMMARY OF THE INVENTION

It would be advantageous to achieve an improved apparatus and system that is capable of automatically producing a mix of two or more food products that fulfils at least two target criteria. In general, the invention preferably seeks to mitigate, alleviate or eliminate one or more of the above mentioned disadvantages singly or in any combination. In particular, it may be seen as an object of the present invention to provide an apparatus and a method that solves the above mentioned problems, or other problems, of the prior art.

To better address one or more of these concerns, in a first aspect of the invention an apparatus is provided for producing a mix of a first type of food products and at least one second type of food products so that the mix fulfils at least two target criteria including weight ratio criterion indicating the weight ratio between the first and the at least one second type of food products in the mix and lean/fat ratio criterion of the mix, comprising:

- at least one conveyor means having an in-feed end and an out-feed end, the out-feed end being directed to a destination area,
- at least three controllable in-feed channels arranged at the in-feed end of the at least one conveyor means for supplying separate streams of the first and second food products where at least one of the in-feed channels supplies the first type of food products and at least two of the in-feed channels supply the second type of food products, the at least two in-feed channels supplying the second type of food products being distinguished via different lean/fat ratio estimates,
- at least one lean/fat ratio measuring means for determining the lean/fat ratio of the food products,
- means for determining the weight of the food products.
- a control unit for utilizing the determined weight of food products and the measured lean/fat ratio of the food products as operation parameters in operating the in-feeding of the at least three controllable in-feed channels so that the mix fulfills the at least two target criteria.

Thus, an apparatus is provided that is not only capable of producing mix of highly accurate lean/fat ratio but also where the weight ratio of the at least two product types is fulfilled. The fact that the process is fully automatized means that the throughput is significantly increased since there is no longer need for extra manpower to measure the lean/fat ratio manually and to adjust the lean/fat ratio based thereon, which can be very time consuming and results in a less throughput of the process.

In one embodiment, said mix has additional third target criterion being target weight of the mix. Accordingly, the fact that the above mentioned weight ratio of the at least first and second food product types and the lean/fat ratio may be fully controlled, it is additionally possible to reach a target weight value of the mix.

In one embodiment, the at least one conveyor means includes a first conveyor and a second conveyor and where the out-feed ends of the first and second conveyors are directed to said destination area, said at least two of the in-feed channels supplying the second type of food products being arranged at the in-feed end of the second conveyor and said at least one in-feed channel supplying the first type of food product being arranged at the in-feed end of the first conveyor.

In one embodiment, said at least one lean/fat ratio measuring means comprises a first lean/fat ratio measuring means arranged between the in-feed end and the out-feed end of said first conveyor and a second lean/fat ratio measuring means arranged between the in-feed end and the out-feed end of said second conveyor, where the measured first lean/fat ratio value measured by said first lean/fat ratio measuring means and the weight of the first type of food items is used to calculate a real-time operation parameter requesting a lean/fat ratio target value and weight of the second type of food products, said control unit being operable to utilize said operation parameter to operate the outflow of said second type of food products from said at least two in-feed channels to the in-feed end of said second conveyor. Accordingly, information such as the current lean/fat ratio in the mix, or the current lean/fat ratio in the mix and the weight of the first type of food product is in the mix may be used to generate said real-time operation parameter, i.e. what lean/fat ratio is needed at any instant of time to maintain the lean/fat ratio in the mix and also e.g. to maintain the correct weight ratio between the first and the at least one second type of food products in the mix.

In one embodiment, the first type of food product is a frozen trim and the at least one second type of food product is fresh trim.

In one embodiment, said destination area includes a pre-grinder or a take-away conveyor for receiving the food products from said at least one conveyor means and for conveying food products to a grinder. The delivery of the first and the at least one second type of food products, e.g. said fresh and frozen trim is thus delivered to this take away conveyor that conveys them to said grinder where the trim may e.g. be pre-grinded. Therefore, since two (or more) lean/fat ratio measuring means are arranged between the in-feed ends and the out-feed ends of the conveyors an accurate lean/fat ratio of the trim (the food products) in the grinder is known at all times.

In one embodiment, said lean/fat ratio measuring means is an X-ray apparatus. In an embodiment, said X-ray source is a dual wavelength X-ray source of high and low X-rays. A highly accurate method is thus provided, for measuring the lean/fat ratio, also sometimes referred to as chemical lean (CL) of the food products. Referring to the example above, the CL of the frozen trim is thus used as an operation parameter, or to determine an operation parameter, to operate the control of mix of fresh trim, but the fresh trim in the two (or more) in-feed channels may be distinguished between two (or more) different VL, e.g. high VL and low VL, where the high and low VLs are above and below the target CL level of the mix. Thus, the CL of the frozen trim may control the stream of fresh high VL and low VL food products into the X-ray apparatus between the in-feed end and the out-feed end of the second conveyor. There could of course also be several different streams of food products having different VL levels.

In one embodiment, the measured lean/fat ratio of said second type of food products is compared with said lean/fat ratio estimate, where in case of a non-match a feed-back correction command is issued for adjusting the flow of said second type of food products such that the lean/fat ratio of the second type of food products substantially matches with said lean/fat ratio target value. This is of particular advantage because the lean/fat ratio estimate, typically based on VL level, may be partly incorrect and may also vary between different suppliers, e.g. one supplier may sell a trim with a VL estimate 0.6 but another supplier might give this same trim the VL level 0.55. The supplied second type of food products may e.g. come in containers, tub and the like that are marked with said lean/fat ratio estimate, e.g. via barcoding that indicated an estimated VL level of the food products. Accordingly, the control unit, which may be a part of a centralized processor or e.g. be an integral part of the X-ray apparatus, can now adjust the flow in real-time such that the output substantially matches said lean/fat target ratio. This is typically iteration where such a lean/fat target value/operation parameter is at all times, e.g. every second, issued requesting a certain CL level from the second type of food products.

In one embodiment, said means for determining the weight of the food products is based on utilizing the detected intensity detected by said detection means of the high and low X-rays as input in estimating the weight of the food objects. In that way, no additional weighing units are needed since the X-ray may in relatively accurate way determine the weight of the incoming food products.

According to another aspect, the present invention relates to a method for producing a mix of a first type of food products and at least one second type of food products so that the mix fulfils at least two target criteria including weight ratio criterion indicating the weight ratio between the first and the at least one second type of food products in the mix and lean/fat ratio criterion of the mix, comprising:

supplying at least one stream of the first type of food product via at least on in-feed channel, supplying at least two separate streams of the at least one second type of food products via at least two in-feed channels, the separate streams being distinguished via different lean/fat ratio estimates, the at least two separate streams being independently controllable, determining the lean/fat ratio of the food products, determining the weight of the food products, and utilizing the determined weight of food products and the measured lean/fat ratio of the food products as operation parameters in operating the in-feeding of the at least three controllable in-feed channels so that the mix fulfills the at least two target criteria.

In one embodiment of said method, the mix has further third target criterion being target weight of the mix.

According to a third aspect, the present invention further relates to a computer program comprising instructions for carrying out the steps of the above mentioned method steps when said computer program is executed on a suitable computer device.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
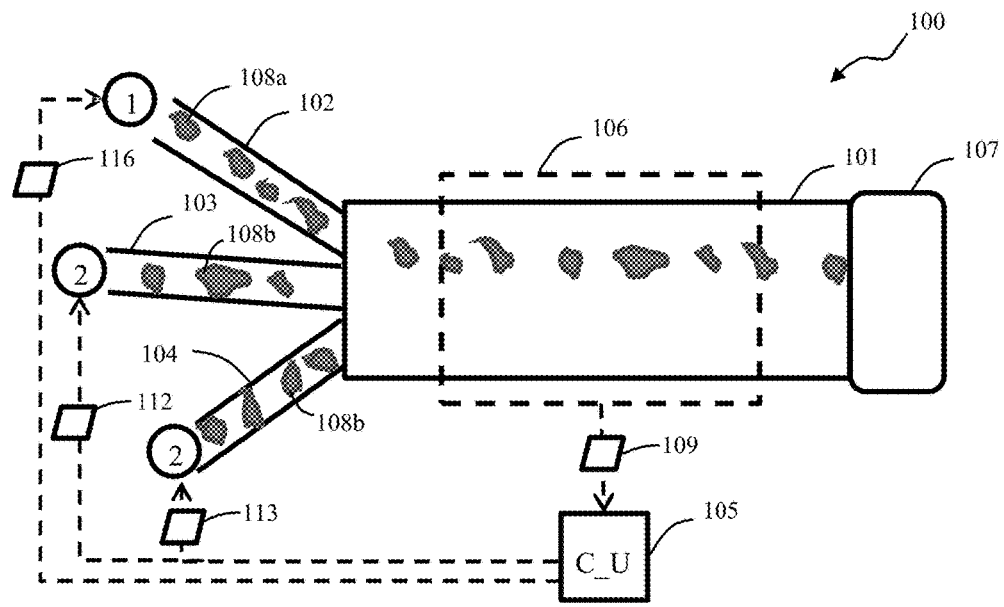
FIGS. 1 and 2 shows two embodiment of an apparatus according to the present invention for producing a mix of a first type of food products and at least one second type of food products so that the mix fulfils at least two target criteria including weight ratio criterion indicating the weight ratio between the first and the at least second type of food products in the mix and lean/fat ratio criterion of the mix.

FIG. 1 shows one embodiment of an apparatus 100 according to the present invention for producing a mix of a first type of food products 108a and at least one second type of food products 108b so that the mix fulfils at least two target criteria including weight ratio criterion indicating the weight ratio between the first and at the least one second type of food products in the mix and lean/fat ratio criterion of the mix. The mix may contain one or more of the food product types selected from, but not limited to, ground products such as ground beef, ground lamb, ground pork, ground poultry, ground fish etc. The apparatus comprises a conveyor means, which as depicted here may be a conveyor 101 comprising a conveyor belt having an in-feed end and an out-feed end where the out-feed end is directed to a destination area 107 such as a pre-grinder or fine-grinder, three controllable in-feed channels 102-104, lean/fat measuring means 106 and a control unit (C_U) 105.

The three controllable in-feed channels 102-104, which may e.g. be conveyors including a conveyor belts, are arranged at the in-feed end of the conveyor 101 for supplying separate streams of the first and at least one second type of food products 108a,b. One of the three in-feed channels 102 supplies the first type of food products and the remaining two in-feed channels supply separate streams of the second type of food products 108b. The two in-feed channels supplying the second type of food products are distinguished via different lean/fat ratio estimates, which may be based on visual loan (VL) where an operator at some prior stage in the processing has estimated the lean/fat ratio visually. For simplicity, it will be assumed that the two separate streams of the second product is high VL (above some pre-fixed threshold) and low VL (below a pre-fixed threshold), where the high and low VLs are above and below the lean/fat target of the mix. Moreover, it will be assumed that the first type of food product is frozen trim 108a and the second type of food product is fresh trim 108b.

The lean/fat ratio measuring means 106 is in one embodiment an X-ray apparatus, such as an X-ray source of dual wavelength of high and low X-rays, comprising an X-ray radiation source positioned above the food products for radiating food products 108a,b with an X-ray beam and a detection means positioned below the food products for detecting the density of the X-rays passing through the food products where the detected intensity is then processed to determine the lean/fat ratio of the food products, often referred to as chemical lean (CL). The measured dual intensity may also be processed so as to determine an estimated weight of the food products.

The control unit (C_U) 105 utilizes the determined weight of food products and the measured lean/fat ratio of the food products as operation parameters in operating the in-feeding of the at least three controllable in-feed channels so that the mix fulfills the at least two target criteria, i.e. the lean/fat ratio and the weight ratio of the first and the second type of food products. As an example, the weight target could be that 60% of the absolute weight of the mix should be fresh trim and 40% of the absolute weight should be frozen trim and the lean/fat ratio could be CL=0.88. A further target of the mix could be the total weight of the mix, e.g. 800 kg, where 480 kg is fresh trim and 320 kg is frozen trim.

In one embodiment, the frozen trim 108a is the "operating stream" where based on the measured lean/fat ratio in the X-ray apparatus for the frozen trim a real-time operation parameter 109 is generated and utilized by the control unit (C_U) 105 to operate the separate streams of the fresh trim 108b. The two in-feed channels 103-104 for the fresh trim 108b are then operated based on operation commands 112, 113, which e.g. trigger start and stop of the in-feed channels with the aim of reaching the above mentioned weight ratio target and lean/fat ratio, and even the total weight of the mix in the mixer 107. The in-feed channel 102 that supplies the first type of food products is also preferably controllable via operation command 116 where the flow of the frozen trim may be adjusted by e.g. slowing it down or stop the flow of the frozen trim, e.g. when said at least two target criteria of the mix has been reached, or e.g. when more fresh trim is needed and less frozen trim.

Since the lean/fat ratio of the fresh trim (i.e. the second food products) is only a visual lean estimate (VL) it is preferred to compare the actual lean/fat ratio measured by e.g. said X-ray apparatus, i.e. the CL value, with the VL value to check whether the VL value is within acceptable uncertainty limit. If it is within acceptable uncertainty limit no correction is needed. However, if the difference between the CL and the VL levels is too large the control unit (C_U) 105 adjusts the flow of the fresh trim accordingly to correct for this difference. Such a feedback correction may be an iteration which is running continuously where this error is compensated with the adjustment in the flow via adjustment of the operation commands 112, 113.

In one embodiment, the X-ray apparatus is further utilized for bone detection and detection of other undesired objects such as metals and cartilage, for both the fresh and frozen trim (both the two or more product types), where rejection mechanism (not shown here) would also be provided for removing these undesired objects prior to entering the mix.

In one embodiment, the means for determining the weight of the food products may, as mentioned above, be based on weighing the summed up weight of the mix and e.g. only the stream of the second food products and determine the weight of the first type of food product by means of subtracting the weight of the second type of food products from the summed up weight. Other types of weighing are of course possible, e.g. the food products may be weight at the in-feed channels by e.g. dynamic weighing apparatus.

Figure 2:
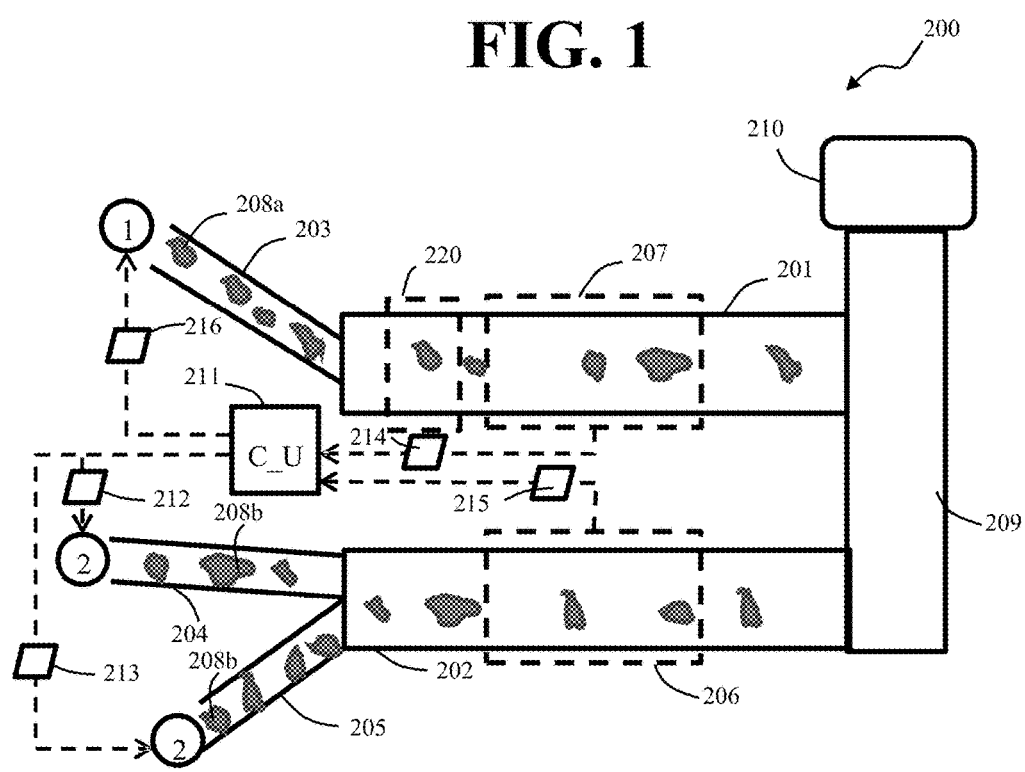

FIG. 2 shows another embodiment of an apparatus 200 according to the present invention where two separate conveyors are utilized, a first conveyor 201 and a second conveyor 202. The out-feed ends of these two conveyors 201, 202 lead to a common destination area 210, which may a pre-grinder, via a take-away conveyor 209, where the food products may be pre-grinded.

Similarly as discussed in relation to FIG. 1, the fat/lean measuring means 206, 207 may be an X-ray apparatus that measures the lean/fat level, often referred to as Chemical Lean level (CL level), which is arranged between the in-feed ends and the out-feed ends of the first and the second conveyors 201, 202, respectively. The first in-feed channel 203 is arranged at the in-feed end of the first conveyor 201 and the two in-feed channels 204, 205 for the second type of food products 208b are arranged at the in-feed end of the second conveyor 202.

The first type of food product 208a is in this embodiment used as the "operated stream" where the measured CL level of the first food product, e.g. frozen trim, is used as real-time operation parameter 214 requesting a CL target level of the second type of food products, e.g. fresh trim. This operation parameter may also be in a form of information indicating as an example the total weight and the average CL level of the first food product type. The weight of the first food product may be of particular relevance when the weight ratio between the first product type and the second product type are relevant. This may as an example be the case where the mix consists of a frozen and fresh trim, e.g. 40% frozen trim vs. 60% of the total weight of 1000 kg with CL level 0.88. Accordingly, the target criteria of the mix is 400 kg frozen trim, 600 kg fresh trim and CL level of the mix is CL=0.88 (i.e. 88% meat and 12% fat).

A control unit (C_U) 211 is provided operable to utilize this operation parameter, e.g. said information, to operate the outflow of the second type of food products 208b from the two in-feed channels 204, 205. Assuming that said information is sent to the control unit (C_U) 211 it may calculate the amount in kilos needed for e.g. the fresh trim and the average CL level that is needed and based thereon generates operation commands 212, 213 that operate the flow from the in-feed channels 204, 205. This operation may e.g. be based on slowing down the conveying speed of the in-feed channels or starting and stopping the flow from the in-feed channels. As already addressed, the two separate streams may be distinguished via their different lean/fat ratio such as high and low VL where the high VL level is above the target CL level of the mix and the low VL level is below the target CL level of the mix. Referring to the example above, if the target level of the mix is 0.88 the high VL level is above 0.88 and the low VL level is below 0.88.

Moreover, the in-feed channel 203 that may supply the frozen trim may be operated via an operation parameter 216, similar as discussed in relation to FIG. 1, e.g. when the at least two target criteria of the mix has been reached, or when more fresh trim is needed to fulfill the weight ratio criterion between the fresh and the frozen trim such as by slowing down the flow of the frozen trim or to stop temporarily the flow of the frozen trim.

Referring to the example above, initially the control unit (C_U) 211 assumes that the VL level of the second type of food products in-feed channels is correct. After conveying several second type of food products through the X-ray apparatus the average CL level of the second type of food products 208b is compared with the VL level of the incoming stream of second food products to check the reliability of the VL level in the in-feed channels. In case of non match, e.g. if the VL level is too far from a pre-determined error window, a feed-back correction command 215 is issued and utilized by the control unit (C_U) 211 for adjusting the flow from the in-feed channels accordingly so that both the weight and the average CL level of the second type of food product matches the required CL level and the weight of the second type of food products. The flow of the first type of food products is preferably run parallel to this, i.e. both the streams of first and second type of food products is run simultaneously. Since the stream of the first type of food products is the "operating stream" it is preferred that the weight target of the first stream is completed before the weight target of the stream of second type of food products is completed so that a final CL level adjustment in the mix can be completed. Assuming that the first type of food product is frozen trim and the second type of food product is fresh trim, a pre-grinder may be provided (not shown) at the first conveyor 201 to separate the frozen trim into smaller frozen trim items, where these smaller trim items are run through the X-ray system. It should be noted that the invention should not be construed as being limited to a single in-feed channel for the first food product and two in-feed channels for the second food product. The first in-feed channel could just as well include two or more first in-feed channels and the two in-feed channels could similarly be three or more in-feed channels. Also, the mix of food products could be e.g. be a mix of three or more food products where the number of conveyors might similarly include three or more conveyors (see embodiment in FIG. 2) or three or more in-feed channels (see embodiment in FIG. 1).

Figure 3:
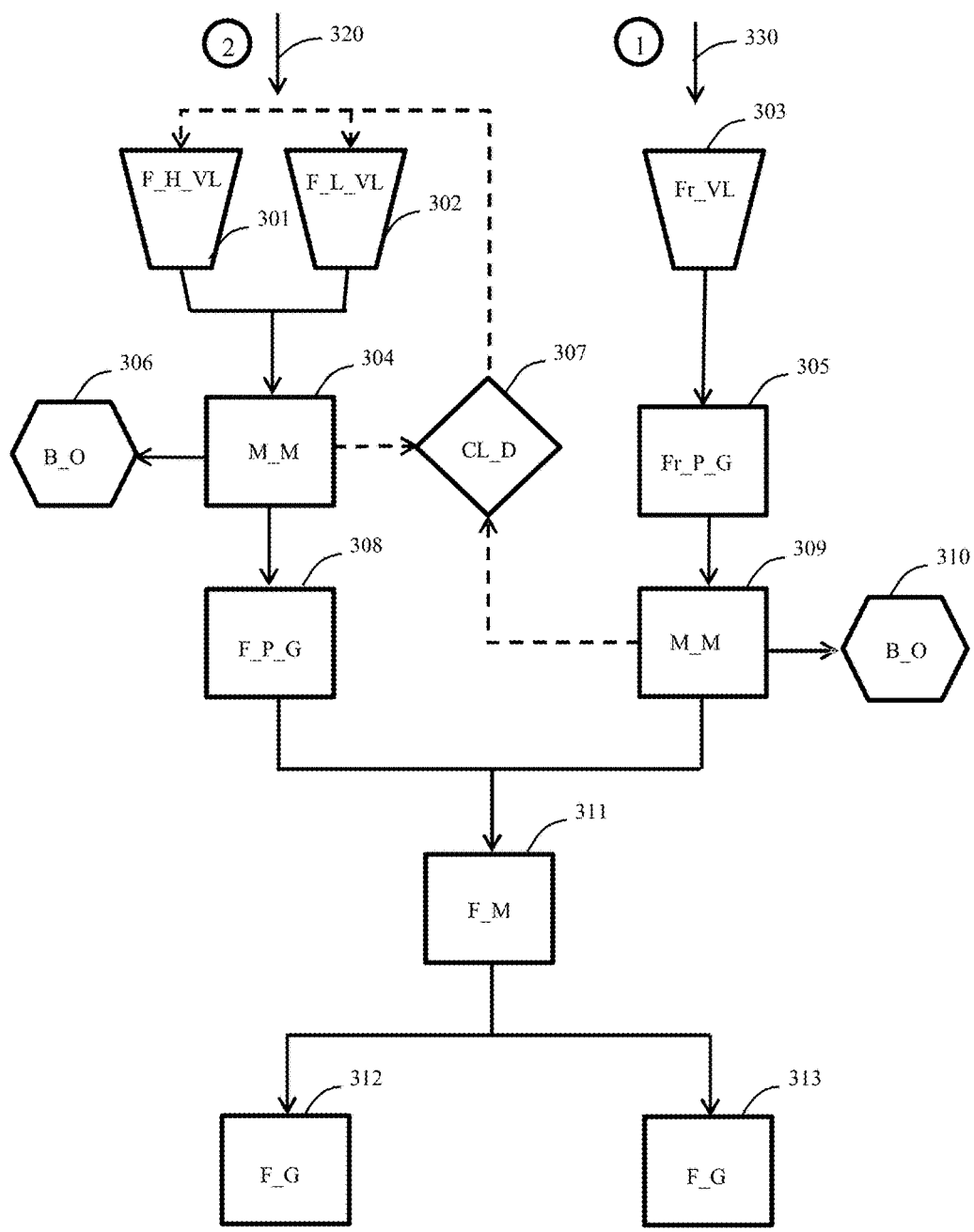
FIG. 3 shows a flowchart of one embodiment of a method according to the present invention for producing a mix of a first type of food products and at least one second type of food products so that the mix fulfils at least two target criteria including weight ratio criterion indicating the weight ratio between the first and the at least second type of food products in the mix and lean/fat ratio criterion of the mix.

FIG. 3 shows an embodiment of a flowchart according to the present invention for producing a mix of a first type of food products and at least one second type of food products so that the mix fulfils at least two target criteria including weight ratio criterion indicating the weight ratio between the first and at least second type of food products in the mix and lean/fat ratio criterion of the mix.

As discussed in relation to FIG. 1, it will be assumed that there are two food product types, frozen trim as first product type and fresh trim as a second product type, where there is a single stream of frozen trim as indicated by arrow 330 and two streams of fresh trim as indicated by arrow 320. The two streams differ in their VL level where one stream may be stream of fresh high VL level (F_H_VL) 301 and the other stream is a stream of fresh low VL level (F_L_VL) 302, where the high and low VLs are selected such that they are above and below the lean/fat target ratio of the mix.

The frozen trim is pre-grinded (Fr_P_G) 305, but this may be necessary if the frozen trim comes in large blocks. The pre-grinded frozen trim is conveyed through a lean/fat measuring means (M_M) 309 such as said X-ray apparatus where, as discussed previously, an accurate CL level is measured and is subsequently conveyed to a final mixer (F_M) 311. Moreover, the X-ray data may be used to detect whether bones or any other undesired objects are present in the trim. If such undesired objects are detected they are removed from the frozen trim stream (B_O) 310.

Based on the measured CL level of the frozen trim a target CL data (CL_D) 307 is issued, a kind of a fresh trim target value or data, and sent to a control unit that utilizes this CL data to operate the flow of the high VL and low VL in-feed channels 301, 302. As discussed in relation to FIG. 2, this data may further include the current weight of the mix and thus include, in addition to the CL level needed from fresh trim, the amount in kg that is needed at each instant of time, but the weight ratio between the frozen and fresh trim may be one of the target value that a customer requires. This data may be considered as a real-time data or commands that is continuously issued and sent to the control unit that utilizes this data to operate the stream of fresh trim from the two in-feed channels.

The accurate CL level of this stream of fresh trim is measured by the X-ray apparatus (M_M) 304, e.g. based on calculating average CL values for each respective stream, where the average CL level is compared with the high/low VL level, i.e. it is checked whether the VL levels are accurate enough. In case of non-match, i.e. because the VL levels are too inaccurate, the in-feeding of the two channels 301, 302 of the fresh trim is adjusted accordingly to compensate for these differences. In case the X-ray apparatus detects bones or any other types of undesired objects they are removed from the fresh trim stream. In this embodiment, the fresh trim is pre-grinded (F_P_G) 308 and subsequently sent to said final mixer where it is mixed with the frozen trim. The final mixer may subsequently output to two or more separate final grinders (F_G) 312, 313.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

What is claimed is:

1. A method for producing a mix of a first type of food products and at least one second type of food products so that the mix fulfils target criteria, the method comprising:
    producing the mix by
        supplying at least one stream of the first type of food products via at least one first in-feed channel, wherein the first type of food products includes frozen trim;
        supplying at least two separate streams of the at least one second type of food products via at least two second in-feed channels, wherein the at least two separate streams of the second type of food products are distinguished from each other based on each of the two separate streams having a different previously-obtained lean/fat ratio estimate, the at least two separate streams being independently controllable, wherein the at least one second type of food products includes fresh trim;
        combining the supplied at least one stream of the first type of food products and the supplied at least two separate streams of the at least one second type of food products;
    wherein producing the mix further includes
        determining the lean/fat ratio of the combined first type of food products and at least one second type of food products, and
        determining the weight of the first type of food products and at least one second type of food products, and
        operating in-feeding of the at least one first in-feed channel and the at least two second controllable in-feed channels in real-time so that the mix fulfils the target criteria by utilizing, as real-time operation parameters,
            the determined weight of the first type of food products and the at least one second type of food products,
            the determined lean/fat ratio of the first type of food products, and
            the lean/fat ratio estimates of each the two separate streams of the second type of food products;
    wherein the target criteria include
        a weight ratio criterion of the weight ratio between the first type of food products and the at least one second type of food products in the mix,
        a frozen/fresh ratio criterion of the mix, and
        a lean/fat ratio criterion of the mix.

2. The method according to claim 1, wherein said mix has an additional target criterion being a target weight of the mix.

3. The method according to claim 1, wherein the step of supplying at least one stream of the first type of food product and the step of supplying at least two separate streams of the at least one second type of food products further includes the step of utilizing at least one conveyor means including a first conveyor and a second conveyor, and
    wherein out-feed ends of the first and second conveyors are directed to a destination area, said at least two of the in-feed channels supplying the second type of food products being arranged at an in-feed end of the second conveyor and said at least one in-feed channel supplying the first type of food product being arranged at an in-feed end of the first conveyor.

4. The method according to claim 3, wherein the step of determining the lean/fat ratio of the first type of food products and the at least one second type of food products further comprises the step of utilizing a first lean/fat ratio measuring means arranged between the in-feed end and the out-feed end of said first conveyor, and a second lean/fat ratio measuring means arranged between the in-feed end and the out-feed end of said second conveyor,
    wherein a measured first lean/fat ratio value measured by said first lean/fat ratio measuring means and the weight of the first type of food products is used to calculate a real-time operation parameter requesting a lean/fat ratio target value and weight of the second type of food products, and
    the method further comprises the step of utilizing a control unit being operable to utilize said operation parameter to operate the outflow of said second type of food products from said at least two in-feed channels to the in-feed end of said second conveyor.

5. The method according to claim 1, wherein said step of determining the lean/fat ratio of the first type of food products and the at least one second type of food products utilizes an X-ray apparatus.

6. The method according to claim 4, further comprising the step of comparing the measured lean/fat ratio of said second type of food products with a lean/fat ratio estimate for said second type of food products,
    wherein in case of a non-match, the method further includes the step of issuing a feed-back correction command that adjusts the flow of said second type of food products such that the lean/fat ratio of the second type of food products substantially matches with said lean/fat ratio target value.

7. The method according to claim 3, wherein said destination area includes a pre-grinder or a take-away conveyor, that receives the first type of food products and the at least one second type of food products from said at least one conveyor means and conveys the first type of food products and the at least one second type of food products to a grinder.

8. The method according to claim 1, wherein the first type of food product is frozen trim and the at least one second type of food product is fresh trim.

9. The method according to claim 5, wherein the step of determining the weight of the first type of food products and the at least one second type of food products further includes the step of utilizing detected intensity of X-rays as input to estimate the weight of the first type of food products and the at least one second type of food products.

10. The method according to claim 9, wherein the X-rays include X-rays of a first wavelength and X-rays of a second wavelength, the first wavelength being higher than the second wavelength.

11. The method according to claim 1, wherein the first type of food product is a first type of meat including beef, pork, lamb, or fish and the at least one second type of food product is a second type of meat including beef, pork, lamb, or fish, the first type of meat being different than the second type of meat.

12. The method according to claim 1, wherein the mix is produced so as to fulfil a target weight criteria, wherein producing the mix further includes operating in-feeding of the at least one first in-feed channel and the at least two second controllable in-feed channels in real-time so that the mix further fulfills the target weight criteria, wherein the target criteria is the total weight of the mix produced.

13. The method according to claim 1, wherein the at least two separate streams include high lean fresh trim and low lean fresh trim, wherein the high lean fresh trim is above a lean/fat target mix threshold and the low lean fresh trim is below the lean/fat target mix.

14. The method according to claim 1, wherein said step of determining the lean/fat ratio of the combined first type of food products and the at least one second type of food products utilizes an X-ray apparatus, and the X-ray apparatus is further configured to detect undesired objects.

15. The method according to claim 1, wherein the step of determining the weight of the first type of food products and the at least one second type of food products further includes using an X-ray apparatus as input to estimate the weight of the first type of food products and the at least one second type of food products, and the X-ray apparatus is further configured to detect undesired objects.

16. The method according to claim 1, wherein the step of determining the weight of the first type of food products and the at least one second type of food products further includes using a dynamic weighing apparatus.

17. The method according to claim 1, wherein said operating in-feeding of the at least first in-feed channel and the at least two second controllable in-feed channels includes slowing an in-feed rate of the at least first in-feed channel or the at least two second controllable in-feed channels.

18. The method according to claim 1, wherein said producing the mix further includes determining in real-time, while producing the mix, the weight of the combined first type of food products and at least one second type of food products.

19. The method according to claim 18, wherein said operating the in-feeding of the at least one first in-feed channel and the at least two second controllable in-feed channels in real-time includes utilizing, as the real-time operation parameters, the determined weight of the combined first type of food products and the at least one second type of food products.

* * * * *